(12) United States Patent
Horn et al.

(10) Patent No.: US 7,323,233 B2
(45) Date of Patent: Jan. 29, 2008

(54) SHEATH MATERIALS AND PROCESSES

(75) Inventors: Daniel James Horn, Shoreview, MN (US); Yiqun Wang, Tokyo (JP); Victor Schoenle, Greenfield, MN (US)

(73) Assignee: Scimed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/256,612

(22) Filed: Sep. 26, 2002

(65) Prior Publication Data
US 2004/0062891 A1    Apr. 1, 2004

(51) Int. Cl.
B32B 1/08   (2006.01)
F16L 11/04  (2006.01)
F16L 11/20  (2006.01)
A61M 29/02  (2006.01)
A61M 39/00  (2006.01)

(52) U.S. Cl. ............... 428/36.9; 428/34.1; 428/35.2; 428/35.7; 428/36.91; 604/19; 604/96.01

(58) Field of Classification Search ........... 428/34.1, 428/35.2, 35.5, 35.7, 36.1, 36.9, 36.91, 36.92; 604/19, 48, 93.01, 96.01
See application file for complete search history.

(56) References Cited

U.S. PATENT DOCUMENTS

| | | | |
|---|---|---|---|
| 3,027,487 A | 3/1962 | Dench | |
| 3,356,108 A | 12/1967 | Johnston | |
| 3,406,685 A | 10/1968 | May | |
| 3,861,972 A | 1/1975 | Glover et al. | |
| 3,969,176 A | 7/1976 | Bassett et al. | |
| 4,418,189 A * | 11/1983 | Morello | 528/345 |
| 4,695,280 A * | 9/1987 | Watanabe et al. | 623/1.54 |
| 5,306,246 A | 4/1994 | Sahatjian et al. | |
| 5,439,447 A | 8/1995 | Miraki | |
| 5,496,275 A | 3/1996 | Sirhan et al. | |
| 5,690,613 A | 11/1997 | Verbeek | |
| 5,860,998 A * | 1/1999 | Robinson et al. | 606/194 |
| 6,027,487 A | 2/2000 | Crocker | |
| 6,110,142 A | 8/2000 | Pinchuk et al. | |
| 6,238,376 B1 | 5/2001 | Peterson | |
| 6,240,231 B1 | 5/2001 | Ferrera et al. | |
| 6,257,800 B1 * | 7/2001 | Masters | 405/224 |
| 6,280,545 B1 | 8/2001 | Kanesaka | |
| 6,322,586 B1 | 11/2001 | Monroe et al. | |
| 6,352,531 B1 | 3/2002 | O'Connor et al. | |
| 2004/0131808 A1 | 7/2004 | Schoenle et al. | |

FOREIGN PATENT DOCUMENTS

WO    WO99/44649    10/1999

OTHER PUBLICATIONS

International Search Report mailed Jan. 30, 2004 for Application No. PCT/US03/29922.

* cited by examiner

Primary Examiner—Rena Dye
Assistant Examiner—Walter B. Aughenbaugh
(74) Attorney, Agent, or Firm—Fish & Richardson P.C.

(57) ABSTRACT

Sheath materials and processes are disclosed. For example, hypotube sheaths and processes of making hypotube sheaths are disclosed. Devices and systems, including medical devices and systems, such as catheters, containing hypotube sheaths are also disclosed.

30 Claims, 3 Drawing Sheets

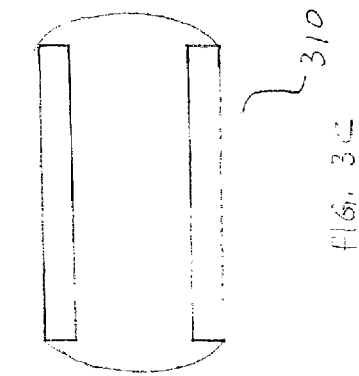
FIG. 3A
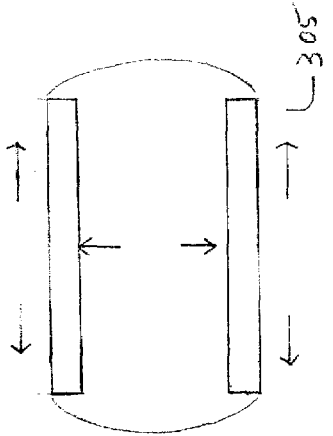
FIG. 3B
FIG. 3C
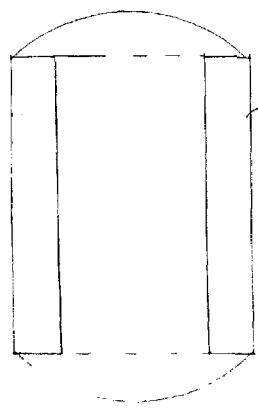
FIG. 3D
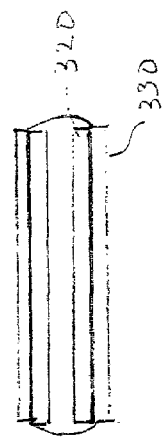
FIG. 3E
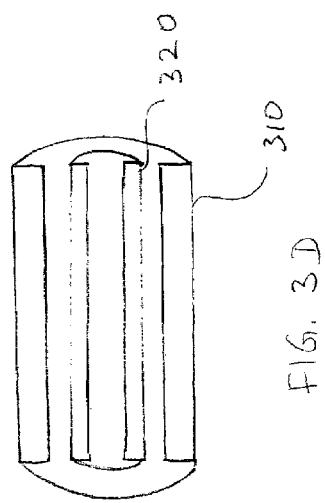

SHEATH MATERIALS AND PROCESSES

TECHNICAL FIELD

The invention relates to sheath materials and processes, such as hypotube sheath materials and hypotube sheath processes.

BACKGROUND

Sheath materials are used in a variety of systems, including, for example, medical devices, such as balloon catheters.

Balloon catheters are commonly used in medical procedures. As an example, in some procedures a balloon catheter is used to open an occluded lumen, as in angioplasty. As another example, in certain procedures a balloon catheter is used to position another medical implement, such as a stent or graft, within a lumen. As an additional example, a balloon catheter can be used to selectively block a passageway. In additional examples, a balloon catheter is used in various combinations of these procedures.

Typically, a balloon catheter is positioned within a blood vessel, and the balloon portion of the catheter is then inflated with an inflation fluid. In some cases, a balloon catheter includes a hypotube. The hypotube is often designed to act as a part of the conduit for the inflation fluid and to impart an appropriate amount of stiffness to the balloon catheter so that the balloon catheter can be positioned (e.g., in a blood vessel) within a patient. Under certain circumstances, it can be desirable to reinforce the hypotube with a sheath.

SUMMARY

The invention relates to sheath materials and processes, such as hypotube sheath materials and hypotube sheath processes.

In one aspect, the invention relates to a method of bonding a material to an article. The method includes longitudinally stretching a tube of the material while heating the tube and pressurizing an interior of the tube, thereby forming a stretch blown-tube of the material. The method also includes shrinking the stretch-blown tube of the material so that the material bonds to a surface of the article.

Embodiments of the methods can include one or more of the following features. The wall thickness of the material in the stretch-blown tube can be, for example, less than the wall thickness of the material in the tube before stretch-blowing. The outer diameter of the material in the stretch-blown tube can be, for example, less than as the outer diameter of the material in the tube before stretch-blowing. The inner diameter of the material in the stretch-blown tube can be, for example, less than the inner diameter of the material in the tube before stretch-blowing. While longitudinally stretching the tube, the tube material can be heated to a temperature, for example, that is at least about 0.85 times the glass transition temperature of the material. While longitudinally stretching the tube, the pressure in the interior of the tube can be, for example, at least about 50 psi. While longitudinally stretching the tube, the longitudinal strain of the tube can be, for example, at least about 110%.

In another aspect, the invention features a device that includes an article having a material bonded to the surface of the article. The material has a post buckle fracture tensile strength of at least about 6500 psi.

In a further aspect, the invention features a device that includes an article having a material bonded to the surface of the article. The material has a tensile strength of at least about 21,000 psi.

In one aspect, the invention features a device that includes an article having a material bonded to the surface of the article. The material has a hoop stress of at least about 3300 psi.

In another aspect, the invention features a device that includes an article having a material bonded to the surface of the article. The material has a load at break ratio of at least about 1.25.

In another aspect, the invention features a device that includes an article having a material bonded to the surface of the article. The material has a hoop stress ratio of at least about 1.25.

In one aspect, the invention features a tube-shaped article having a wall formed of a polymeric material having a post buckle fracture tensile strength of at least about 6500 psi.

In another aspect, the invention features a tube-shaped article having a wall formed of a polymeric material having a tensile strength of at least about 21,000 psi.

In a further aspect, the invention features a tube-shaped article having a wall formed of a polymeric material having a hoop stress of at least about 3300 psi.

In one aspect, the invention features a tube-shaped article having a wall formed of a polymeric material having a load at break ratio of at least about 1.25.

In another aspect, the invention features a tube-shaped article having a wall formed of a polymeric material having a hoop stress ratio of at least about 1.25.

Embodiments can include one or more of the following features.

The device can be a medical device, such as, for example, a balloon catheter.

The article can be a hypotube. The material can be a hypotube sheath material.

The post buckle fracture tensile strength of the material can be at least about 6500 psi (e.g., at least about 7000 psi, at least about 7500 psi).

The material can have a tensile strength of at least about 21,000 psi (e.g., at least about 22,500 psi, at least about 25,000 psi).

The material can have a hoop stress of at least about 3300 psi (e.g., at least about 3500 psi, at least about 3750 psi).

The material can have a load at break ratio of at least about 1.25 (e.g., at least about 1.5, at least about 1.75).

The material can have a hoop stress ratio of at least about 1.25 (e.g., at least about 1.5, at least about two).

The material can be formed of one or more polymers. Examples of polymers include polyamides, copolymers of polyamides, polyesters and copolymers of polyesters.

The sheath can be formed of a relatively strong material (e.g., having a relatively high tensile strength and/or a relatively high hoop stress). This can be advantageous when the sheath is used, for example, as a hypotube sheath because it can assist in reinforcing the hypotube.

The sheath can be formed of a relatively thin material. This can be advantageous when the sheath is used as a hypotube sheath in, for example, a medical device because it can reduce the profile of the medical device. This can, for example, make it easier to position the medical device (e.g., catheter device) within a blood vessel.

The sheath can be formed of a material that is both relatively strong (e.g., having a relatively high tensile strength and/or a relatively high hoop stress) and relatively thin. This can be advantageous when the sheath is used as a hypotube sheath in, for example, a medical device because it can reduce the profile of the medical device and assist in reinforcing the hypotube.

The methods can allow for a relatively high degree of flexibility in preparing a sheath (e.g., a hypotube sheath). For example, the parameters (e.g., longitudinal strain, pressure, temperature) used in the processes can be selected so that both the inner diameter and the outer diameter of the tube decrease. As another example, the parameters can be selected so that the outer diameter of the tube remains substantially unchanged while the inner diameter of the tube is increased. As a further example, the parameters can be selected so that the outer diameter of the tube decreases while the inner diameter of the tube remains substantially unchanged. Typically, the process parameters are selected so that the wall thickness of the sheath after processing (e.g., after stretch-blowing) is less than the wall thickness of the sheath before processing.

Features and advantages are in the description, drawings and claims.

DESCRIPTION OF DRAWINGS

FIGS. 3A-3E are cross-sectional views of an embodiment of a process for bonding a sheath to a hypotube.

DETAILED DESCRIPTION

In general, the sheaths can be used in a variety of systems and devices. For example, the sheaths can be used in medical systems and devices, such as balloon catheters, stent delivery systems, angiographic catheters, etc.

Figure 1:
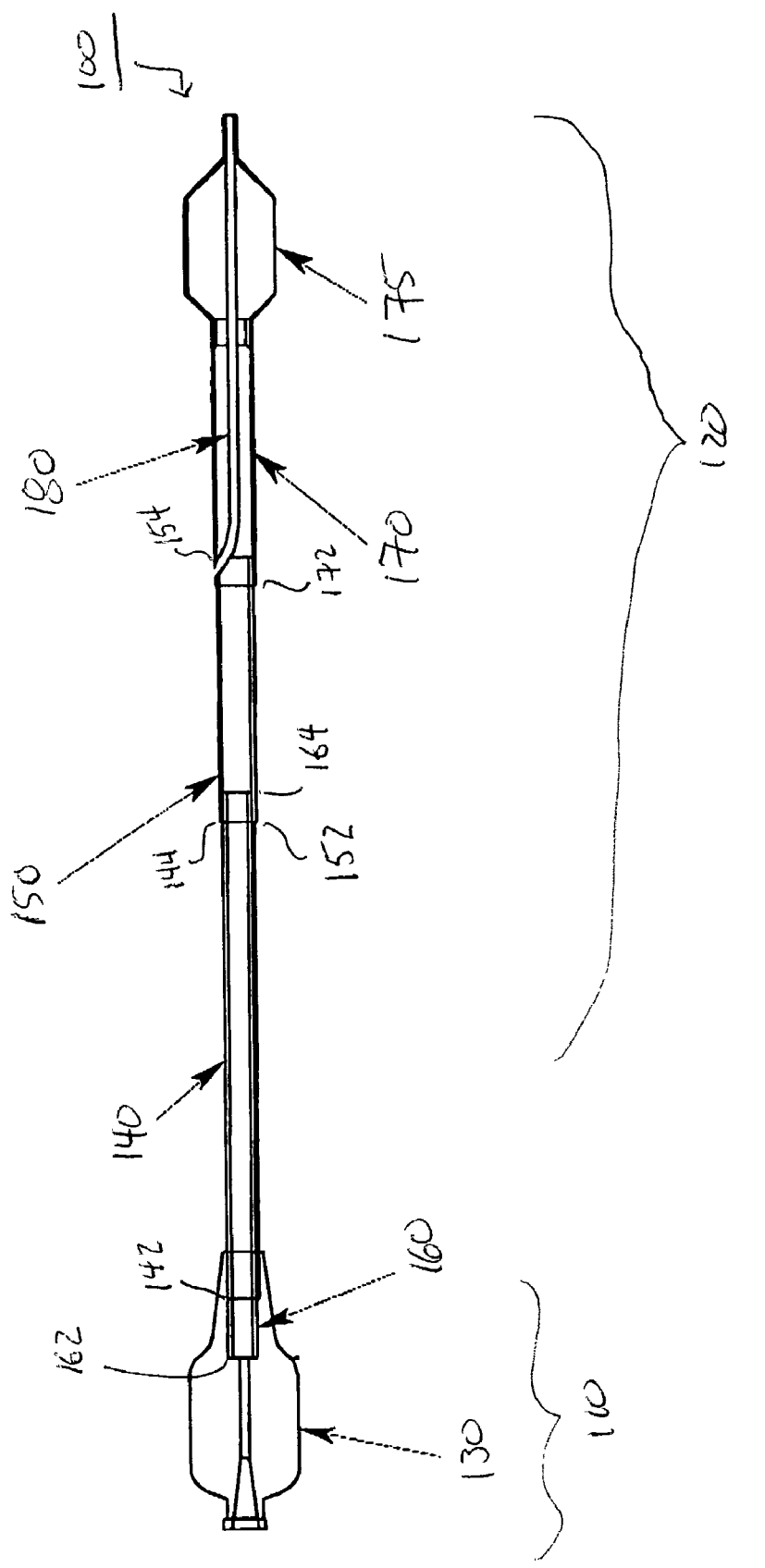
FIG. 1 is a cross-sectional view of an embodiment of a balloon catheter.

FIG. 1 is a cross-sectional view of a balloon catheter 100 having a proximal end 110, which generally remains outside the body, and a distal end 120. Balloon catheter 100 includes a manifold 130, a sheath 140 having proximal end 142 and distal end 144, a midshaft 150 having a proximal end 152 and a distal end 154, a hypotube 160 having a proximal end 162 and a distal end 164, a distal shaft 170 having a proximal end 172 and a lumen 180 for a guidewire, and a balloon 175. Sheath 140 surrounds and is bonded to a portion of hypotube 160. Sheath 140 is also bonded to midshaft 150, and midshaft 150 is also bonded to a distal shaft 170. Balloon catheters having this general configuration are known. Examples of such commercially available balloon catheters include the Monorail® family of balloon catheters (Boston Scientific-SciMed, Maple Grove, Minn.).

Figure 2:
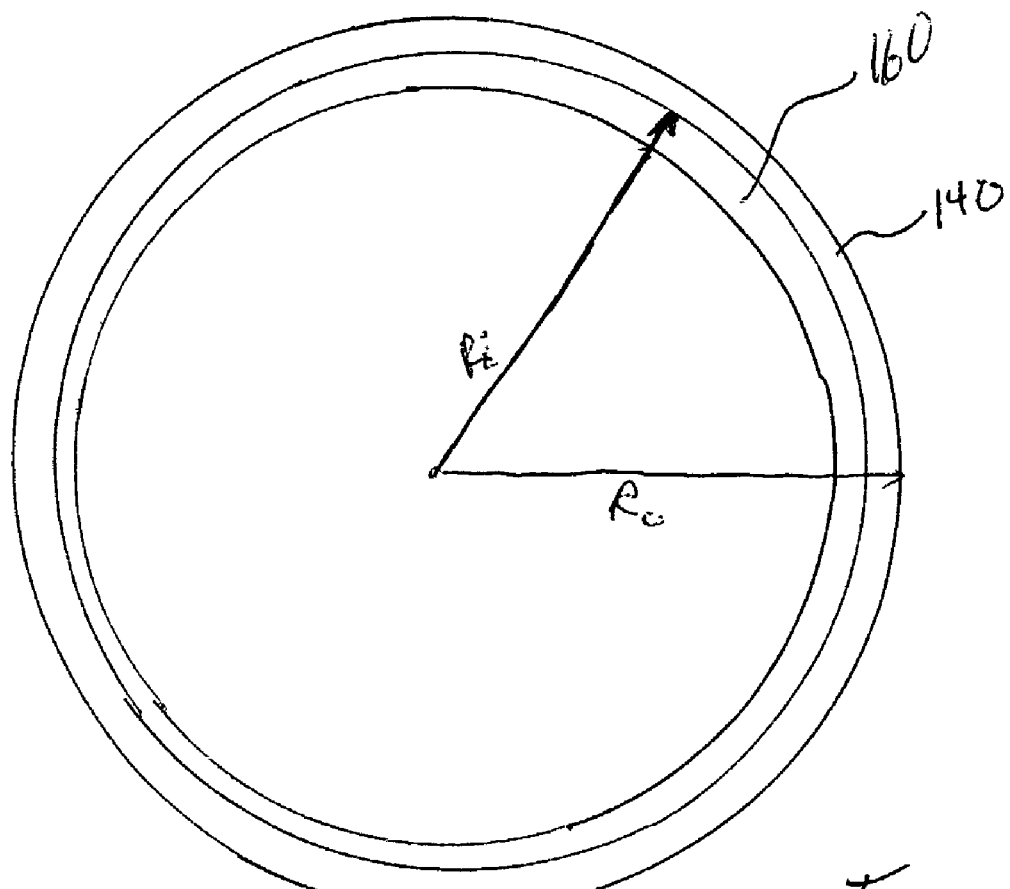
FIG. 2 is a cross-sectional view of an embodiment of a hypotube and hypotube sheath as indicated in FIG. 1.

Referring to FIG. 2, the inner diameter ($R_1$), outer diameter ($R_O$), and wall thickness ($R_O-R_1$) of sheath 140 can generally be varied as desired. In some embodiments, however, it may be desirable for sheath 140 to be relatively thin because, for example, this can reduce the profile of balloon catheter 100. For example, sheath 140 can have a wall thickness of about 0.005 inch or less (e.g., about 0.004 inch or less, about 0.0035 inch or less, about 0.003 inch or less, about 0.0025 inch or less, about 0.002 inch or less, about 0.0015 inch or less, about 0.001 inch or less). Typical values for the inner diameter of sheath 140 are from about 0.02 inch to about 0.03 inch (e.g., from about 0.022 inch to about 0.0265 inch), and typical values for the outer diameter of sheath 140 are from about 0.025 inch to about 0.035 inch (e.g., from about 0.028 inch to about 0.032 inch).

The strength of sheath 140 can also generally be varied as desired. But, in certain embodiments, it can be desirable for sheath 140 to be relatively strong because, for example, this can enhance the ability of sheath 140 to reinforce hypotube 160. Parameters that can be used to measure the strength of sheath 140 include, for example, tensile strength and hoop stress.

In certain embodiments, sheath 140 has a tensile strength of at least about 21,000 pounds per square inch (psi) (e.g., at least about 22,500 psi, at least about 25,000 psi, at least about 27,500 psi, at least about 30,000 psi). As referred to herein, the tensile strength of a hypotube sheath is determined by dividing the load at break of the hypotube sheath by the cross-sectional area of the hypotube sheath, where the cross-sectional area of the hypotube sheath is equal to $\pi(R_O-R_1)^2$.

In general, the load at break of sheath 140 can be varied as desired. Typically, the load at break for sheath 140 is at least about two pounds (e.g., at least about three pounds, from about three pounds to about five pounds, from about three pounds to about four pounds). As referred to herein, the load at break of a hypotube sheath is determined as follows. The sheath material is bonded (e.g., heat shrunk) to a wire (e.g., a copper wire with a silver coating), and a longitudinal strain is applied to the wire to reduce the diameter of the wire, thereby removing the sheath material from the wire. Opposite ends of an about three inch long sample of the removed sheath material are placed in grips that are about two inches apart from each other. The grips are pulled apart at a strain rate of about three inches per minute until the sheath breaks, and the load on the sample as the sheath breaks is the load at break.

In certain embodiments, sheath 140 has a post buckle fracture tensile strength of at least about 6500 psi (e.g., at least about 7000 psi, at least about 7500 psi, at least about 8000 psi). As referred to herein, the post buckle fracture tensile strength of a hypotube sheath is determined by dividing the post buckle fracture load at break of the hypotube sheath by the cross-sectional area of the hypotube sheath, where the cross-sectional area of the hypotube sheath is equal to $\pi(R_O-R_1)^2$.

In general, the post buckle fracture load at break of sheath 140 can be varied as desired. Typically, the post buckle fracture load at break for sheath 140 is at least about one pound (e.g., at least about two pounds, from about two pounds to about five pounds, from about two pounds to about four pounds). As referred to herein, the post buckle fracture load at break of a hypotube sheath is determined as follows. Opposite ends of a sample having a length of about 3.5 inches and formed of sheath bonded to hypotube are placed in grips that are about two inches apart from each other. The grips are compressed until the distance between the grips is about 0.3 inch at a rate of about six inches per minute to buckle the sample. The buckled sample is removed from the grips and straightened so that the hypotube is broken in two separate pieces with each piece of the hypotube still being bonded to the sheath. Opposite ends of the sample are placed in the grips (two inches apart) and pulled apart at a strain rate of about three inches per minute until the sheath breaks. The load on the sample as the sheath breaks is the post buckle fracture load at break.

In certain embodiments, sheath 140 has a hoop stress of at least about 3300 psi (e.g., at least about 3500 psi, at least about 3750 psi, at least about 4000 psi, at least about 4250 psi, at least about 4500 psi, at least about 4750 psi, at least about 5000 psi). As referred to herein, the hoop stress of a hypotube sheath is equal to $P(R_1^2+R_O^2)/(R_O^2-R_1^2)$, where P is the burst pressure of the hypotube sheath.

In general, the burst pressure of sheath 140 can be varied as desired. Typically, sheath 140 has a burst pressure of at least about 300 psi (e.g., at least about 400 psi, from about 400 psi to about 700 psi, from about 500 psi to 600 psi). As referred to herein, the burst pressure of a hypotube sheath refers to the internal pressure at which the hypotube sheath bursts. The burst pressure of a hypotube sheath is determined by measuring the internal pressure of the hypotube sheath as the hypotube sheath (after being removed from the hypotube) is inflated at a rate of two psi per second with a 10 second hold at every 50 psi interval until the hypotube sheath bursts.

The burst diameter ($D_{burst}$) of sheath 140 can also be varied as desired. In certain embodiments, sheath 140 has a burst diameter of at least about 0.02 inch (e.g. at least about 0.025 inch, at least about 0.03 inch). As referred to herein, the burst diameter of a hypotube sheath is the outer diameter of the hypotube sheath at burst. The burst diameter of a hypotube sheath is determined by measuring the diameter of the hypotube sheath as the hypotube sheath is inflated at a rate of two psi per second with a 10 second hold at every 50 psi interval until the hypotube sheath bursts. The diameter is measured using a hand held micrometer snap gauge during the 10 second hold periods.

In some embodiments, the change in distention of sheath 140 is less than about 0.003 inch (e.g., less than about 0.002 inch, from about 0.001 inch to about 0.002 inch). As referred to herein, the change in distention of a hypotube sheath is equal to $D_{burst}-D_{initial}$, where $D_{initial}$ is the outer diameter of the hypotube sheath prior to inflation.

Typically, sheath 140 is formed of a polymer, such as a thermoplastic elastomer (e.g., a heat shrinkable polymer). Examples of polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters (e.g., polyetheretherketones (PEEKs), polyurethanes, polyethylenes, polypropylenes, copolymers and ionomers of ethylene, copolymers and ionomers of polypropylene, polystyrenes and copolymers of polystyrenes. Examples of commercially available polyesters include the Selar PT family of polymers (e.g., Selar PT 8307, Selar PT4274, Selar PTX280), which are commercially available from E. I. DuPont de Nemours (Wilmington, Del.), the Cleartuf family of polymers (e.g., Cleartuf 8006), which are commercially available from M&G Polymers (Apple Grove, W.Va.), the Traytuf family of polymers (e.g., Traytuff 1006), which are commercially available from the Shell Chemical (Houston, Tex.), the Melinar family of polymers, commercially available from E. I. DuPont de Nemours (Wilmington, Del.), the Celanex family of polymers, commercially available from Ticona (Summit, N.J.), the Riteflex family of polymers, commercially available from Ticona (Summit, N.J.), the Hytrel family of polymers (e.g., Hytrel 5556, Hytrel 7246, Hytrel 4056), commercially available from E. I. DuPont de Nemours (Wilmington, Del.), the Arnitel family of polymers (e.g., Arnitel EM630), commercially available from DSM (Erionspilla, Ind.). Examples of commercially available polyamides include Nylon 12, commercially available from Atofina (Philadelphia, Pa.), Nylon 6, commercially available from Honeywell (Morristown, N.J.), Nylon 6/10, commercially available from BASF (Mount Olive, N.J.), Nylon 6/12, commercially available from Ashley Polymers (Cranford, N.J.), Nylon 11, Nylon MXD-6, and the Grivory family of polymers, commercially available from EMS (Sumter, S.C.), the Grilamid family of polymers (e.g., Grilamid L25, Grilamid L20), commercially available from EMS (Sumter, S.C.), the Vestamid family of polymers (e.g., Vestamid L2101F), commercially available from Daicel-Degussa Ltd., and the PEBAX family of polymers (e.g., PEBAX 5533, PEBAX 2533, PEBAX 7033), commercially available from Atofina (Philadelphia, Pa.), the Trogamid family of polyamides from Daicel-Degussa, Crystamid MS1100 from Atofina (Philadelphia, Pa.), and Vestamid L2101F nylon 12 from Degussa AG. An example of a commercially available polyethylene is Marlex 4903 high density polyethylene from Phillips 66 (Bartlesville, Okla.).

Manifold 130 is generally designed to connect balloon 175 to an inflation device.

In general, hypotube 160 is designed to act as a part of the conduit for the inflation fluid and to impart an appropriate amount of stiffness to balloon catheter 100 so that balloon catheter 100 can be positioned (e.g., in a blood vessel) within a patient. Hypotube 160 is typically made of a metal or an alloy. Examples of hypotube materials include nitinol and stainless steel (e.g., 303, 304, 316L). While the dimensions of hypotube 160 can be varied depending upon the intended use, hypotube 160 usually has an outer diameter of about 0.02 inch to about 0.03 inch (e.g., about 0.0236 inch, about 0.0264 inch) and a wall thickness of about 0.003 inch or greater.

Midshaft 150 is generally designed to act as an additional portion of the conduit for the inflation fluid. Midshaft 150 is typically made of a material that is softer and or more flexible than the material from which hypotube 160 is formed. Typically, midshaft 150 has a Shore D hardness of about 72 or more. Midshaft 150 can be formed, for example, of a polymer (e.g., one or more of the polymers disclosed herein for use as a hypotube sheath material). Usually, midshaft 150 has an outer diameter of from about 0.025 inch to about 0.035 inch (e.g., about 0.034 inch) and an inner diameter of from about 0.02 inch to about 0.3 inch (e.g., about 0.265 inch). In certain embodiments, the inner diameter and/or outer diameter of midshaft 150 can be tapered.

Generally, distal shaft 170 is designed to act as an additional portion of the conduit for the inflation fluid. Distal shaft 170 is typically made of a material that is softer and or more flexible than the material from which midshaft 150 is formed. Typically, distal shaft 170 has a Shore D hardness of about 70 or less. Distal shaft 170 can be formed, for example, of a polymer (e.g., one or more of the polymers disclosed herein for use as a hypotube sheath material). In some embodiments, the inner and outer diameter of distal shaft 170 taper (i.e., decrease going from the proximal end of distal shaft 170 to the distal end of distal shaft 170). As an example, the proximal end of shaft 170 can have an outer diameter of 0.0357 inch and an inner diameter of about 0.0283 inch, and the distal end of distal shaft 170 can have an outer diameter of about 0.0321 inch and an inner diameter of about 0.0263 inch. In certain embodiments, distal shaft 170 is untapered (e.g., with an outer diameter of from about 0.035 inch to about 0.4 inch, such as about 0.037 inch, and an inner diameter of from about 0.0275 inch to about 0.0325 inch, such as about 0.0296 inch).

Guidewire lumen 180 is designed to house a guidewire. The guidewire is typically formed of a metal or alloy and is used to provide the appropriate amount of stiffness to balloon catheter 100 while it is being positioned within a patient. A portion of the guidewire is disposed within lumen 180, and a portion of the guidewire is disposed along the outer surface of midshaft 150 and sheath 140 (e.g., so that this portion of the guidewire is disposed inside of a guide catheter surrounding distal end 120 of balloon catheter 100).

Balloon 175 can be made of any material appropriate for use in the balloon of a balloon catheter. Typically, balloon 175 is made of one or more layers of polymeric materials. Typical polymeric materials include polyesters and polyamides. Exemplary materials are disclosed, for example, in co-pending and commonly owned U.S. patent application Ser. No. 09/798,749, filed on Mar. 2, 2001, and entitled "Multilayer Medical Device," which is hereby incorporated by reference.

FIGS. 3A-3E show an embodiment for bonding a sheath to a hypotube. As shown in FIG. 3A, a tube 300 of sheath material is provided. For example, tube 300 can be formed by extrusion. A longitudinal strain, heat and internal pressure are then applied to the tube. This process is referred to herein as stretch-blowing the tube. FIG. 3B shows an intermediate tube 305 formed part way through the stretch-blowing process. The longitudinal strain applied to the tube is indicated by the horizontal arrows, and the internal pressure applied to the tube is indicated by the vertical arrows. The longitudinal strain, pressure and temperature are ultimately reduced to provide a stretch-blown tube 310 of sheath material having an outer diameter that is smaller than the outer diameter of tube 300 and an inner diameter that is smaller than the inner diameter of tube 300 (FIG. 3C). A hypotube 320 is placed within stretch-blown tube 310 (FIG. 3D), and stretch-blown tube 310 is heated so that its inner diameter decreases, resulting in a sheath 330 of sheath material bonded (e.g., heat shrunk) to hypotube 320 (FIG. 3E).

While FIGS. 3A-3E shown an embodiment of a process for bonding a sheath to a hypotube, other embodiments are possible. In general, the parameters selected during the process can be varied as desired. As an example, the parameters (e.g., longitudinal strain, pressure, temperature) can be selected so that stretch-blown tube 310 of sheath material has an outer diameter that is substantially the same as the outer diameter of tube 300 and an inner diameter that is larger than the inner diameter of tube 300. As another example, the parameters (e.g., longitudinal strain, pressure, temperature) can be selected so that stretch-blown tube 310 of sheath material has an outer diameter that is smaller than the outer diameter of tube 300 and an inner diameter that is substantially the same as the inner diameter of tube 300.

Without wishing to be bound by theory, it is believed that there are some general trends that depend upon the values of certain parameters (e.g., longitudinal strain, temperature and pressure) used when stretch-blowing the tube. The general trends include the following. For a given tube material and desired dimensions for the intermediate tube, increasing the value of one parameter allows for the use of lower values for one or both of the other parameters. For a given material, pressure and longitudinal strain, increasing the temperature results in an intermediate tube with a larger outer diameter, and the resulting intermediate tube tends to undergo a greater degree of shrinkage during the process of bonding (e.g., heat shrinking) to the hypotube. For a given material, pressure and longitudinal strain, decreasing the temperature results in an intermediate tube with a smaller outer diameter, and the resulting intermediate tube tends to undergo a smaller degree of shrinkage during the process of bonding (e.g., heat shrinking) to the hypotube. For a given material, temperature and pressure, increasing the longitudinal strain results in an intermediate tube with a smaller inner diameter, and the resulting intermediate tube tends to undergo a smaller degree of shrinkage during the process of bonding (e.g., heat shrinking) to the hypotube. For a given material, temperature and pressure, decreasing the longitudinal strain results in an intermediate tube with a larger inner diameter, and the resulting intermediate tube tends to undergo a greater degree of shrinkage during the process of bonding (e.g., heat shrinking) to the hypotube. For a given material, temperature and longitudinal strain, increasing the pressure results in an intermediate tube with a larger outer diameter, and the intermediate tube tends to undergo a greater degree of shrinkage during the process of bonding (e.g., heat shrinking) to the hypotube. For a given material, temperature and longitudinal strain, decreasing the pressure results in an intermediate tube with a smaller outer diameter, and the intermediate tube tends to undergo a smaller degree of shrinkage during the process of bonding (e.g., heat shrinking) to the hypotube.

When stretch-blowing a tube of sheath material, the temperature of the sheath material should be sufficient to allow the material from which the tube is made to undergo the desired change in dimensions (e.g., to elongate and/or become thinner). The temperature can be varied from, for example, below the glass transition temperature of the material ($T_g$) from which the tube is formed up to about 0.9 times the melt temperature ($T_m$) of the material from which the tube is formed, where $T_m$ is measured in Kelvin. For example, the temperature used during stretch-blowing can be at least about $0.85T_g$ (e.g., from about $0.85T_g$ to about $1.2T_g$, from about $0.85T_g$ to about $1.1T_g$, from about $0.85T_g$ to about $T_g$), where $T_g$ is measured in Kelvin. As referred to herein, the glass transition temperature of a sheath material (e.g., a polymer) is determined according to ASTM D1356, and the melt temperature of a sheath material (e.g., a polymer) is determined according to DIN 16770D2. As an example, Vestamid L2101F nylon 12 (Degussa AG) has a $T_g$ of about 333K and a $T_m$ of about 518K, and a temperature of about 318K can be used for this material during stretch blowing, corresponding to about $0.95T_g$ and about $0.6T_m$.

In embodiments in which a sheath material is formed of a block copolymer, the glass transition temperature and melt temperature of the sheath material refer to the glass transition temperature and melt temperature of the block within the block copolymer that has the highest glass transition temperature and melt temperature. For example, PEBAX 6333 (Atofina) is a block copolymer that contains blocks of nylon 12, and nylon 12 is the block with the highest glass transition temperature and melt temperature in PEBAX 6333. Thus, as referred to herein, the glass transition temperature and melt temperature of PEBAX 6333 correspond to the glass transition temperature and melt temperature of the nylon 12 blocks in PEBAX 6333. Accordingly, PEBAX 6333 has a $T_g$ of about 333K and a $T_m$ of about 445K, and a temperature of about 318K can be used for this material during stretch blowing, corresponding to about $0.95T_g$ and about $0.7T_m$.

In certain embodiments, the temperature of the material during stretch-blowing is not measured directly. For example, during stretch-blowing, the material may be present in an oven for a period of time. The temperature of the material can be inferred from the period of time the material spent in the oven and the physical characteristics (e.g., heat capacity, thermal conductivity) of the material. The temperature of the material can also be inferred by comparing the properties of the stretch-blown material to those of the stretch-blown material achieved under conditions where the temperature of the material during stretch-blowing is known. For example, the temperature can be inferred by comparing the properties of a stretch-blown material to those of the stretch-blown material achieved when the material is held in a constant temperature bath (e.g., constant temperature water bath) during stretch-blowing The longitudinal strain applied to the tube when stretch-blowing the tube should be sufficient to allow the material from which the tube is made to undergo the desired change in dimensions (e.g., to elongate and/or become thinner). Typically, the longitudinal strain is at least about 110% (e.g., at least about 120%, at least about 130%, at least about 140%, at least about 150%), where the percent longitudinal strain corresponds to the increase in the length of the tube due to stretch-blowing the tube. For example, 150% longitudinal strain refers to the stretch-blown tube having a length that is 1.5 times the length the tube had just before being stretch-blown.

The internal pressure of the tube during stretch-blowing should be sufficient for the material from which the tube is made to undergo the desired change in dimensions (e.g., to elongate and/or become thinner). Typically, the internal pressure is at least about 50 psi (e.g., at least about 75 psi, at least about 100 psi, at least about 125 psi, at least about 150 psi).

Without wishing to be bound by theory, it is believed that the process described herein can result in a relatively strong hypotube sheath. In particular, it is believed that the use of a longitudinal strain during the stretch-blowing portion of the process, ultimately results in a hypotube sheath that is relatively thin, but that has, for example, a burst pressure and/or load at break that is comparable to those achieved by hypotube sheath preparation processes that result in relatively thick hypotube sheaths (e.g., processes in which a longitudinal strain is not used). It is believed that this results in a relatively thin hypotube sheaths that have relatively large tensile strengths and/or relatively large hoop stresses.

As an example, a sheath material can have a tensile strength ratio of at least about 1.25 (e.g., at least about 1.5, at least about 1.75, at least about two, at least about 2.25). As used herein the tensile strength ratio of a sheath material is determined by dividing the tensile strength of the material as a hypotube sheath (according to the procedure described above) to the tensile strength of the material before being stretch blown (e.g., as an extruded tube).

As another example, a sheath material can have a hoop stress ratio of at least about 1.25 (e.g., at least about 1.5, at least about two, at least about 2.5, at least about three). As used herein, the hoop stress ratio of a sheath material is determined by dividing the hoop stress of the material as a hypotube sheath (according to the procedure described above) to the hoop stress of the material before being stretch blown (e.g., as an extruded tube).

Without wishing to be bound by theory, it is further believed that the process described herein for bonding a hypotube sheath to a hypotube can result in a hypotube sheath having a polymer chain profile in which the polymer chains are substantially axially oriented (e.g., with the degree of axial orientation generally increasing from the outer radius of the hypotube sheath to the inner radius of the hypotube sheath).

The following examples are illustrative and not intended to be limiting.

EXAMPLES

Tables I and II list average values for certain parameters determined for multiple specimens of different hypotube hypotube sheath samples. "O.D." refers to the average outer diameter of the hypotube sheaths of the corresponding specimens in units of inches. "I.D." refers to the average inner diameter of the hypotube sheaths of the corresponding specimens in units of inches. "Thickness" refers to the average wall thickness [(outer diameter minus inner diameter)/2] of the hypotube sheaths of the corresponding specimens in units of inches. "Area" refers to the average cross-sectional area (pi multiplied by the square of the wall thickness) of the hypotube sheaths of the corresponding specimens in units of square inches. "Post Load" refers to the average post buckle fracture load at break of the hypotube sheaths of the corresponding specimens in units of pounds. "Post Tensile" refers to the post buckle fracture average tensile strength of the hypotube sheaths of the corresponding specimens units of pounds per square inch. "Load" refers to the load at break of the hypotube sheaths of the corresponding specimens in units of pounds. "Tensile" refers to the average tensile strength of the hypotube sheaths of the corresponding specimens units of pounds per square inch. "Distention" refers to the average change in outer diameter of the hypotube sheaths (outer diameter at burst minus outer diameter prior to inflation) of the corresponding specimens in units of inches. "Diameter" refers to the average burst diameter of the hypotube sheaths of the corresponding specimens in units of inches. "Pressure" refers to the burst pressure the hypotube sheaths of the corresponding specimens in units of psi. "Stress" refers to the burst stress of the hypotube sheaths of the corresponding samples in units of psi.

TABLE I

| Sample | O.D. | I.D. | Thickness | Area | Post Load | Post Tensile |
|---|---|---|---|---|---|---|
| A | 0.0302 | 0.022 | 0.0041 | $3.362 \times 10^{-4}$ | 1.37 | 4075 |
| B | 0.028 | 0.0234 | 0.0023 | $1.857 \times 10^{-4}$ | 1.200 | 6462 |
| C | 0.0296 | 0.0264 | 0.0016 | $1.407 \times 10^{-4}$ | 1.920 | 13642 |
| D | 0.0316 | 0.0264 | 0.0026 | $2.369 \times 10^{-4}$ | 4.420 | 18660 |
| E | 0.03038 | 0.02393 | 0.003225 | $2.751 \times 10^{-4}$ | 4.850 | 17628 |
| F | 0.02891 | 0.02394 | 0.002485 | $2.063 \times 10^{-4}$ | 3.794 | 18391 |
| G | 0.0294 | 0.0264 | 0.0015 | $1.322 \times 10^{-4}$ | 1.48 | 11195 |

TABLE II

| Sample | O.D. | I.D. | Thickness | Distention | Diameter | Load | Tensile | Pressure | Stress |
|---|---|---|---|---|---|---|---|---|---|
| H | 0.0291 | 0.0262 | 0.0015 | 0.0015 | 0.0306 | 3.78 | 31659 | 535 | 5123 |
| I | 0.0282 | 0.0236 | 0.0023 | 0.0012 | 0.0247 | 2.47 | 15129 | 572 | 3197 |
| J | 0.0274 | 0.0232 | 0.0021 | 0.0013 | 0.0244 | 3.62 | 20030 | 529 | 3239 |

Sample A was a Multi-Link Plus™ hypotube (Guidant, Santa Clara, Calif.) modified as follows. A Multi-Link Plus™ hypotube was cut to isolate a specimen formed from the proximal portion of the device containing only the sheath bonded to the hypotube. Three specimens of sample A were tested. The average values of certain parameters determined for the specimens of sample A are listed in Table I.

Sample B was an AVE S7 hypotube (Medtronic AVE, Santa Rosa, Calif.) modified as follows. An AVE S7 hypotube was cut to isolate a specimen formed from the proximal portion of the device containing only the sheath (PEBAX 7233) bonded to the hypotube. Two specimens of sample B were tested. The average values of certain parameters determined for the specimens of sample B are listed in Table I.

Sample C was prepared as follows. An extruded sheath of Vestamid L2101 F Nylon 12 (Degussa AG) having an outer diameter of about 0.0350 inch and an inner diameter of about 0.0276 inch was stretch-blown under a longitudinal strain of 220% and an internal pressure of 208 psi. During stretch-blowing, the sheath material passed through an 18 inch oven at a temperature of about 63° C. over a period of about 8.9 seconds. It is believed that the sheath material reached a temperature of about 40° C. to about 45° C. during stretch-blowing. A 304L stainless steel hypotube having an outer diameter of about 0.0264 inch and an inner diameter of about 0.020 inch was inserted inside the stretched and blown sheath, and the sheath was bonded (heat shrunk) to the hypotube by heating to a temperature of about 113° C. for at least 30 minutes. Ten specimens of sample C were tested, and the average values of certain parameters determined for the specimens of sample C are listed in Table I.

Sample D was prepared as follows. An extruded sheath of Vestamid L2101 F Nylon 12 (Degussa AG) having an outer diameter of about 0.0380 inch and an inner diameter of about 0.0270 inch was stretch-blown under a longitudinal strain of 190% and an internal pressure of 288 psi. During stretch-blowing, the sheath material passed through an 18 inch oven at a temperature of about 68° C. over a period of about 17.1 seconds. It is believed that the sheath material reached a temperature of about 40° C. to about 45° C. during stretch-blowing A 304L stainless steel hypotube having an outer diameter of about 0.0264 inch and an inner diameter of about 0.020 inch was inserted inside the stretched and blown sheath, and the sheath was bonded (heat shrunk) to the hypotube by heating to a temperature of about 113° C. for at least about 30 minutes. Five specimens of sample D were tested, and the average values of certain parameters determined for the specimens of sample D are listed in Table I.

Sample E was prepared as follows. An extruded sheath of PEBAX 7233 (Atofina) having an outer diameter of about 0.035 inch and an inner diameter of about 0.024 inch was stretch-blown under a longitudinal strain of 150% and an internal pressure of 278 psi. During stretch-blowing, the sheath material passed through an 18 inch oven at a temperature of about 68° C. over a period of about 19.5 seconds. It is believed that the sheath material reached a temperature of about 40° C. to about 45° C. during stretch-blowing. A 304L stainless steel hypotube having an outer diameter of about 0.0237 inch and an inner diameter of about 0.0175 inch was inserted inside the stretched and blown sheath, and the sheath was bonded (heat shrunk) to the hypotube by heating to a temperature of about 113° C. for at least about 30 minutes. Five specimens of sample E were tested, the average values of certain parameters determined for the specimens of sample E are listed in Table I.

Sample F was prepared as follows. An extruded sheath of 95% Vestamid L2101 F Nylon 12 (Degussa AG)/5% PEBAX 7233 (Atofina) having an outer diameter of about 0.0340 inch and an inner diameter of about 0.0240 inch was stretch-blown under a longitudinal strain of 150% and an internal pressure of 268 psi. During stretch-blowing, the sheath material passed through an 18 inch oven at a temperature of about 68° C. over a period of about 19.5 seconds. It is believed that the sheath material reached a temperature of about 40° C. to about 45° C. during stretch-blowing. A 304L stainless steel hypotube having an outer diameter of about 0.0237 inch and an inner diameter of about 0.0175 inch was inserted inside the stretched and blown sheath, and the sheath was bonded (heat shrunk) to the hypotube by heating to a temperature of about 113° C. for about 30 minutes. Five specimens of sample F were tested, and the average values of certain parameters determined for the specimens of sample F are listed in Table I.

Sample G was prepared as follows. An extruded sheath of PEBAX 6333 (Atofina) having an outer diameter of about 0.034 inch and an inner diameter of about 0.0280 inch was stretched and blown under a longitudinal strain of 155% and an internal pressure of 145 psi. During stretch-blowing, the sheath material passed through an 18 inch oven at a temperature of about 68° C. over a period of about 18.9 seconds. It is believed that the sheath material reached a temperature of about 40° C. to about 45° C. during stretch-blowing. A 304L stainless steel hypotube having an outer diameter of about 0.0264 inch and an inner diameter of about 0.020 inch was inserted inside the stretched and blown sheath, and the sheath was bonded (heat shrunk) to the hypotube by heating to a temperature of about 113° C. for at least about 30 minutes. Five specimens of sample G were tested, and the average values of certain parameters determined for the specimens of sample G are listed in Table I.

Sample H was prepared as follows. An extruded sheath of Vestamid L2101 F Nylon 12 (Degussa AG) having an outer diameter of about 0.0380 inch and an inner diameter of about 0.0320 inch was stretched and blown under a longitudinal strain of 220% and an internal pressure of 142 psi. During stretch-blowing, the sheath material passed through an 18 inch oven at a temperature of about 63° C. over a period of about 8.9 seconds. It is believed that the sheath material reached a temperature of about 40° C. to about 45° C. during stretch-blowing. A 304L stainless steel hypotube having an outer diameter of about 0.0264 inch and an inner diameter of about 0.0200 inch was inserted inside the stretched and blown sheath, and the sheath was bonded (heat shrunk) to the hypotube by heating to a temperature of about 113° C. for at least about 30 minutes. Five specimens of sample H were tested, and the average values of certain parameters determined for the specimens of sample H are listed in Table II.

Sample I was a Multi-Link Plus™ hypotube (Guidant, Santa Clara. Calif.) modified as follows. A Multi-Link Plus™ hypotube was cut to isolate a specimen formed from the proximal portion of the device containing only the sheath bonded to the hypotube. 10 specimens of sample A were tested. Three specimens of sample I were tested. The average values of certain parameters determined for the specimens of sample I are listed in Table II.

Sample J was AVE S7 hypotube (Medtronic AVE, Santa Rosa. Calif.) modified as follows. An AVE S7 hypotube was cut to isolate a specimen formed from the proximal portion of the device containing only the sheath (PEBAX 7233) bonded to the hypotube. Two specimens of sample J were tested. The average values of certain parameters determined for the specimens of sample J are listed in Table II.

While certain embodiments have been disclosed, the invention is not so limited.

As an example, the sheath hypotube combination can be used in balloon catheter systems as described above but without also including a midshaft. For example, referring to FIG. 1, a similar balloon catheter can be made to balloon catheter 100 but without midshaft 150 by extending the length of hypotube sheath 140 to the proximal end 172 of distal shaft 170. This could be done, for example, without changing the length of hypotube 160 (e.g., without extending distal end 162 of hypotube 160). Such a balloon catheter could be potentially offer the advantage, for example, of a reduced profile.

As another example, the hypotube sheath can be used in any desired medical device system, including balloon catheters having various designs, such as over-the-wire balloon catheters.

As a further example, the sheath material can be used in other parts of a catheter balloon, such as, for example, to bond outer and inner tubes of a balloon dilation catheter, to form a sheath over various components of an infusion catheter, as part of the material of the balloon of a balloon catheter, as a sheath to connect the catheter forming portion and a hub forming portion of a catheter-hub assembly, to bond a wire to a hypotube, and/or to join two or more hypotubes (e.g., to join a polymer hypotube to a metal hypotube).

As an additional example, as noted above, the sheath material and processes can be used in a variety of systems, including medical device systems and devices. Generally, the sheath materials and/or processes can be used in any system in which it is desirable to bond two or more components together, particularly where it is advantageous to use relatively strong and/or thin materials to provide the bond between the components. Examples of additional systems include electrical systems (to join electrical components), optical systems (e.g., to join fiber optic cables), packaging, and protective covering over pipes used in flow lines.

As yet another example, a tube of a pre-stretch-blown (e.g., extruded) sheath material and/or a tube of a stretch-blown sheath material can have any desired length and/or cross-sectional shape (e.g., circular, square, triangular, rectangular). Moreover, a pre-stretch-blown (e.g., extruded) sheath material and/or a stretch-blown sheath material need not be in the form of a tube. For example, the material(s) can be in the form of a mat or a sheet (e.g., a flat mat, a flat sheet, a partially rolled mat, a partially rolled sheet).

Other embodiments are in the claims.

What is claimed is:

1. A device, comprising:
   a hypotube having a surface; and
   a material bonded to the surface of the hypotube, wherein:
     the material comprises a polymer selected from the group consisting of polyamides and copolymers of polyamides;
     the material has a post buckle fracture tensile strength of at least about 7000 psi; and
     the device is a medical device.

2. The device of claim 1, wherein the device is a balloon catheter.

3. The device of claim 1, wherein the post buckle fracture tensile strength of the material is at least about 7500 psi.

4. The device of claim 1, wherein the material has a tensile strength of at least about 21,000 psi.

5. The device of claim 1, wherein the material has a hoop stress of at least about 3300 psi.

6. The device of claim 1, wherein the material has a tensile strength of at least about 22,500 psi.

7. The device of claim 1, wherein the material has a tensile strength of at least about 25,000 psi.

8. The device of claim 1, wherein the material has a hoop stress of at least about 3500 psi.

9. The device of claim 1, wherein the material has a hoop stress of at least about 3750 psi.

10. The device of claim 1, wherein the material has a load at break ratio of at least about 1.25.

11. The device of claim 1, wherein the material has a load at break ratio of at least about 1.5.

12. The device of claim 1, wherein the material has a load at break ratio of at least about 1.75.

13. The device of claim 1, wherein the material has a hoop stress ratio of at least about 1.25.

14. The device of claim 1, wherein the material has a hoop stress ratio of at least about 1.5.

15. The device of claim 1, wherein the material has a hoop stress ratio of at least about two.

16. A device, comprising:
    a hypotube having a surface; and
    a hypotube sheath material bonded to the surface of the hypotube, wherein;
      the hypotube sheath material comprises a polymer selected from the group consisting of polyamides and copolymers of polyamides;
      the hypotube sheath material has a post buckle fracture tensile strength of at least about 7000 psi; and
      the device is a medical device.

17. The device of claim 16, wherein the device is a balloon catheter.

18. The device of claim 16, wherein the post buckle fracture tensile strength of the material is at least about 7500 psi.

19. The device of claim 16, wherein the material has a tensile strength of at least about 21,000 psi.

20. The device of claim 16, wherein the material has a hoop stress of at least about 3300 psi.

21. The device of claim 16, wherein the material has a tensile strength of at least about 22,500 psi.

22. The device of claim 16, wherein the material has a tensile strength of at least about 25,000 psi.

23. The device of claim 16, wherein the material has a hoop stress of at least about 3500 psi.

24. The device of claim 16, wherein the material has a hoop stress of at least about 3750 psi.

25. The device of claim 16, wherein the material has a load at break ratio of at least about 1.25.

26. The device of claim 16, wherein the material has a load at break ratio of at least about 1.5.

27. The device of claim 16, wherein the material has a load at break ratio of at least about 1.75.

28. The device of claim 16, wherein the material has a hoop stress ratio of at least about 1.25.

29. The device of claim 16, wherein the material has a hoop stress ratio of at least about 1.5.

30. The device of claim 16, wherein the material has a hoop stress ratio of at least about two.

* * * * *

UNITED STATES PATENT AND TRADEMARK OFFICE
CERTIFICATE OF CORRECTION

| | | |
|---|---|---|
| PATENT NO. | : 7,323,233 B2 | Page 1 of 1 |
| APPLICATION NO. | : 10/256612 | |
| DATED | : January 29, 2008 | |
| INVENTOR(S) | : Daniel J. Horn, Yiqun Wang and Victor Schoenle | |

It is certified that error appears in the above-identified patent and that said Letters Patent is hereby corrected as shown below:

Column 3, lines 49-50, "Referring to FIG. 2, the inner diameter ($R_1$), outer diameter ($R_o$), and wall thickness ($R_o - R_1$)" should read --Referring to FIG. 2, the inner radius ($R_i$), outer radius ($R_o$), and wall thickness ($R_o - R_i$)--.

Column 4, line 12 and line 37, "$\pi(R_o-R_1)^2$" should read --$\pi(R_o^2-R_i^2)$--.

Column 4, line 63, "$P(R_1^2 + R_o^2)/(R_o^2-R_1^2)$" should read --$P(R_i^2 + R_o^2)/(R_o^2-R_i^2)$--.

Column 10, lines 13-14, "(pi multiplied by the square of the wall thickness)" should read --(pi multiplied by the difference between the square of the outer radius and the square of the inner radius)--.

Signed and Sealed this

Twenty-second Day of July, 2008

JON W. DUDAS
*Director of the United States Patent and Trademark Office*